United States Patent [19]
Yerfino et al.

[11] Patent Number: 5,993,417
[45] Date of Patent: Nov. 30, 1999

[54] DISPOSABLE SYRINGE WITH AN AUTOMATICALLY RETRACTABLE HYPODERMIC NEEDLE

[76] Inventors: Daniel Alberto Yerfino, Esquiú863, (7600), Mar del Plata, Argentina; Aldo Luis Ducler, Corrientes 415, 6°Floor, Buenos Aires, Argentina

[21] Appl. No.: 09/005,681

[22] Filed: Jan. 13, 1998

[30] Foreign Application Priority Data

Jan. 6, 1998 [AR] Argentina .................. P98 01 00041

[51] Int. Cl.⁶ ...................................................... A61M 5/00
[52] U.S. Cl. ............................................ 604/110; 604/195
[58] Field of Search .................................... 604/195, 110, 604/192, 198, 263, 187

[56] References Cited

U.S. PATENT DOCUMENTS

| | | |
|---|---|---|
| 5,152,750 | 10/1992 | Haining . |
| 5,190,526 | 3/1993 | Murray et al. . |
| 5,222,944 | 6/1993 | Harris . |
| 5,320,606 | 6/1994 | Jore . |
| 5,324,265 | 6/1994 | Murray et al. . |
| 5,382,235 | 1/1995 | Sak . |
| 5,518,370 | 5/1996 | Wang et al. . |
| 5,578,015 | 11/1996 | Robb . |
| 5,616,134 | 4/1997 | Firth et al. . |
| 5,656,031 | 8/1997 | Thorne et al. . |

OTHER PUBLICATIONS

"Maxxon Safety Syringe", prod3.htm en www.stockprofiles.com (http://www.stockprofiles.com/mxon/prod3.htm), pp. 1–2, Jan. 28, 1998.

*Primary Examiner*—John D. Yasko
*Attorney, Agent, or Firm*—Finnegan, Henderson, Farabow, Garrett & Dunner, L.L.P.

[57] ABSTRACT

A disposable syringe with an automatically retractable hypodermic needle of the type consisting of an injector plunger, a container cylinder with needle-carrier head and a needle with connection ferrule. The ferrule is housed in an inner hollow of the head of the cylinder, wherein the tube of the needle has passing axially though it a guiding channel to the outside, the hollow having a plurality of elastic retention tabs and the rear face of the needle-carrier head of the cylinder being in contact with an elastomeric washer interposed in an annular manner between it and the plunger which is defined by a cover whose attack front part has a slightly conical circular crown coinciding with said elastomeric washer and which is equipped centrally with a frustoconical core coinciding in a closely fitting manner with the opening of the ferrule of the needle. The cover also has a perimeter groove on its surrounding face which can be locked in terms of position in a plurality of domed projections of the inner wall of the tube which contains it, thereby forming the shaft of the plunger, the head of the cover and the base of said shaft being joined together by a tensioned elastic means and comprising, in the rear zone of their surrounding wall, a plurality of grooves in the rear zone which link its inside to the outside space.

4 Claims, 2 Drawing Sheets

DISPOSABLE SYRINGE WITH AN AUTOMATICALLY RETRACTABLE HYPODERMIC NEEDLE

The present patent of invention, which is now being filed, the relevant registration being applied for, relates to a disposable syringe, with an automatically retractable hypodermic needle, which is suitable for injecting medicinal substances and/or taking samples of blood and liquids in general, in human or veterinary medicine, with the particular functional characteristic of, once the operation has been completed, producing, by means of a slight additional pressure at the end of the path of the plunger, the automatic firing of the needle in the entering direction, said needle remaining definitively inside it so as to guard against pricking the person handling it and to prevent the latter coming into contact with pathogenic substances which still remain unused, to prevent reuse.

After the procedures referred to above, hypodermic needles usually remain wedged in the ejector tips of the syringes, representing a significant risk of infection for persons responsible for handling them, since combined with their capacity to graze is the fact that they retain dangerously contaminating residues. To protect the staff involved, use is made of container receptacles designed to remove them and store them inside, after which they are transported with other residues for incineration in specially constructed furnaces. However, such operations continue to pose a risk because disposal is not immediate, especially in operating theaters where the surgeon involved is concentrating his attention on the operating area, involuntarily taking his attention away from the action of disposing of said elements once they have been used. Moreover, those responsible for removing the containers referred to are exposed to subsequent accidents owing to the fact that uncovered needles usually pass through their walls and to the fact that the actual operation of inserting them or placing a cap on them represents an additional risk.

Another potential act which poses a threat to the required aseptic measures arises from the fraudulent act which may be committed by any person attempting to reuse syringes with a needle, causing severe harm to subsequent patients which is beyond the control of those responsible.

In view of the aforesaid, it would appear ideal to have a syringe/needle unit which can be deactivated definitively and without the possibility of being rearmed, the needle being protected immediately at the end of the plunger's path, as part of the operation.

In precise terms, the disposable syringe with an automatically retractable hypodermic needle, which is the subject of the invention, tends to optimize the use of such elements, overcoming the drawbacks mentioned and complying with the ideal conditions mentioned in the above paragraph.

Specifically, this is a syringe formed by a hollow cylinder within which the corresponding plunger slides in a closely fitting manner, equipped, respectively, with rear gripping fins and outer thrust enlargement, as in conventional syringes. Said cylinder is notable in that, at its actuator end, it has a needle guide with a projecting axial cylindrical orifice and, on the inside, a core with a frustoconical hollow equivalent to the connection ferrule thereof with elastic retention tabs at its major base and an elastomeric washer on which the head of the plunger is seated.

Said plunger, for its part, is a hollow cylinder whose particular form arises from the fact that it has a blind attack end formed by a cover which is grooved at the perimeter on its outer surrounding face, said groove fixing its original position, on domed embossments of the inner face of the tube containing it, being retained axially at its end by an annular entrant flange of the latter. The attack front part of said cover is a circular crown with a slight conicity which coincides with the elastomeric washer of the container cylinder, with a blind frustoconical tip, equivalent to the opening of the connection ferrule of the needle, while, on the inside, said cover is joined to the base of the plunger by means of an elastic means which is tensioned in its original position.

The unit described is presented, for use, with the hypodermic needle, projecting via its end, covered by a standard cap, with its connection ferrule positioned in the cavity of the core of the cylinder of the syringe and retained by the elastic tabs with no possibility of backward movement, while the plunger is seated with its attack front part on the corresponding face of the elastomeric washer with its frustoconical tip facing the opening of the needle without penetrating totally into it. In order to pick up the substance to be injected from its container or to remove biological samples, the plunger is slid along in the same way as in known syringes, the protective needle cap previously having been removed. In order to inject the medicinal substance or to deposit the sample removed into laboratory test tubes, the procedure is also as with known syringes, i.e. the plunger is pushed in the entering direction as far as the end of its path, its attack front part being again in contact with the elastomeric washer. This arrangement leads to actuation of the novel security device, merely by exerting a pressure which is slightly greater than that required by the previous operation, as a continuation thereof. This gives rise to squashing of the elastomeric washer and therefore the travel of the plunger continues until its frustoconical tip is inserted into the connection ferrule of the needle, wedging itself securely. As a result of precise dimensioning, said frustoconical tip, at the end point of its displacement, causes the total opening-out of the tabs for retaining the needle which, given their contact edge, which has a slope similar to that of the frustoconical tip, allow their insertion and transverse folding, by means of elasticity, toward coincident hollows of the core. At this point, the slight residual advance which the elastomeric washer allows the cylindrical tube of the plunger wedged inside the ferrule of the needle brings about the disconnection of the perimeter groove of the cover and the domed reliefs of the tube, leaving the cover exposed to the retractile force of the elastic means joining to the base, entraining the needle inward in a definitive manner. The retractile displacement of the needle takes place strictly linearly on account of the fact that it is guided in a stable manner by the tube of the plunger vis-à-vis the cover to which it is secured and, at the beginning, also by the guide of the cylinder.

Without altering the functional principle described, which in itself constitutes the novel advantage of the present invention, complementary alternatives which enhance its efficiency are envisaged in the form of the inclusion of an elastic membrane, positioned in the needle guide, which is perforated by the tube of the needle and, when the needle is withdrawn, acts, given the elasticity of its material, as a valve to retain the minute amount of liquid which may have been left inside it; the presence of longitudinal grooves on the surrounding face of the frustoconical tip of the plunger which allows the total passage of liquid to the tube of the needle, when the latter has been wedged; and a reduction in the external diameter of the tubular body of the plunger in its distal portion so as to reduce its zone of friction with the syringe cylinder, thereby creating between both of them a chamber which communicates with the outside via its distal end and with the inside of the plunger through orifices in its tubular wall in order to give rise to a rapid escape of the air which is compressed on account of the rapid backward movement of the cover.

In order to give material form to the advantages discussed briefly in this way and in order to facilitate understanding of the structural and functional characteristics of the disposable syringe with an automatically retractable hypodermic needle, a description is given below of a preferred embodiment and of variants which are illustrated diagrammatically and without a specific scale on the attached sheets, with the express clarification that, precisely because this is an example, it cannot be attributed a limiting or exclusive nature, its purpose simply being to be a mere illustration of the basic underlying design.

In all the figures, the same or equivalent parts or elements which make up the chosen unit as an example for the present explanation correspond to identical reference numbers.

Figure 1:
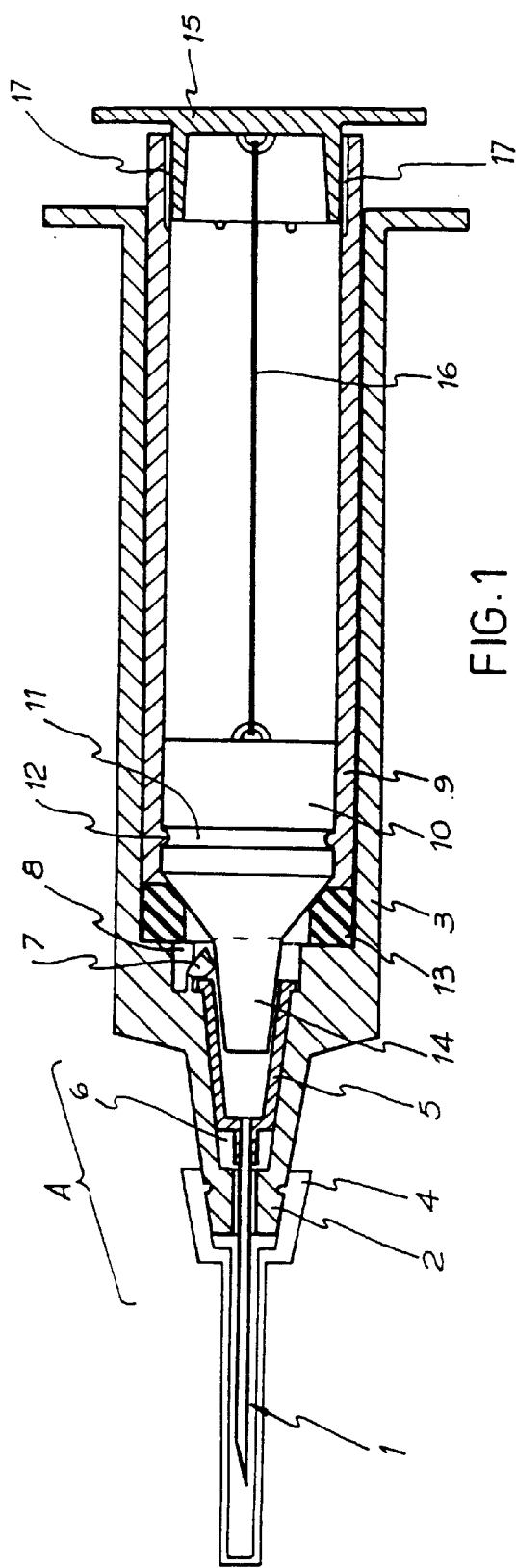
FIG. 1 is a sectional view through a radial plane of the invented unit, with its components positioned as presented for use.

As shown in FIG. 1, the unit is presented with the needle 1 projecting via the guide 2 of the cylinder 3, with its protective cap 4 and its connection ferrule 5 housed in the hollow 6, retained by the elastic tabs 7, of which only one is shown in the figure, capable of folding in the radial direction into the cavities 8. The plunger 9, for its part, is presented with its cover 10 locked by means of its perimeter groove 11 on the domed projections 12 and its attack front part resting on the elastomeric washer 13, the frustoconical tip 14, partially inserted into the opening of said ferrule 5, remaining in this position without being in contact with the ferrule or with the tabs 7. Between said cover 10 and the base 15 of the plunger is the elastic means 16, under tension.

Figure 2:
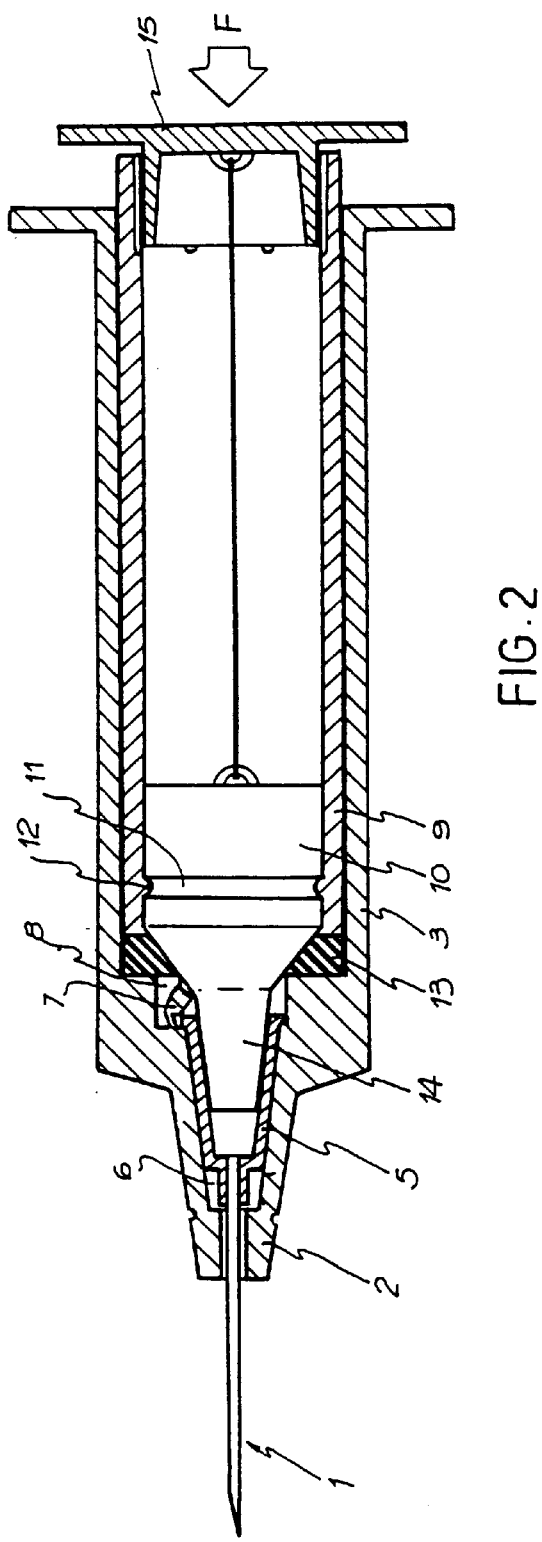
FIG. 2 is a view equivalent to the previous view, with the plunger at the end of its path and the safety device about to be fired.

Injection of the medicinal liquid having taken place by means of customary actuation, or the extracted material having been discharged into the relevant test tubes, the syringe returns to the initial position (FIG. 1) and, through the effect of an additional pressure in the direction F, as may be seen in FIG. 2, the elastomeric washer 13 is squashed, thereby allowing the plunger to advance until its frustoconical tip 14 is secured in the ferrule 5 by means of wedging, opening up the tabs 7 to release the ferrule at the same time as the cover 10 reaches the limit of its path, although its container tube is able to squash said elastomeric washer further, this counter-positioning of effects bringing about disconnection of the perimeter groove 11 from the domed projections 12, said cover being retracted through the action of the elastic means 16, entraining the needle 1 with it which remains housed definitively inside the tubular body of the plunger 9. During the rapid retractile actuation described, the mass of air contained between the head of the cover 10 and the base of the plunger 15 escapes via the grooves 17.

Figure 3:
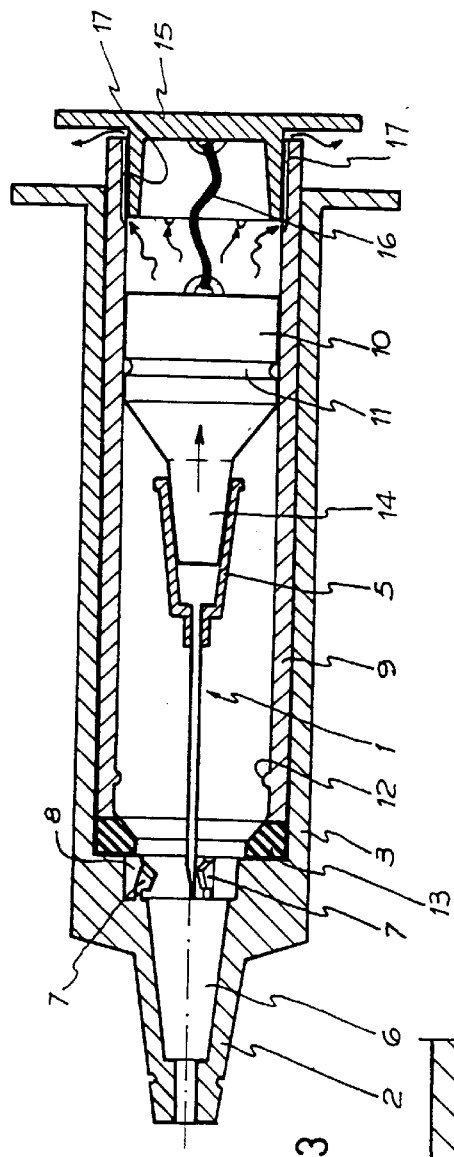
FIG. 3 is a view equivalent to the above views, with the safety device being actuated.

FIG. 3 shows the behavior of the cover in its backward movement, its escape of air and the distension of the elastic means 16, the unit being in such a condition that it may be disposed of and is risk free.

Figure 4:
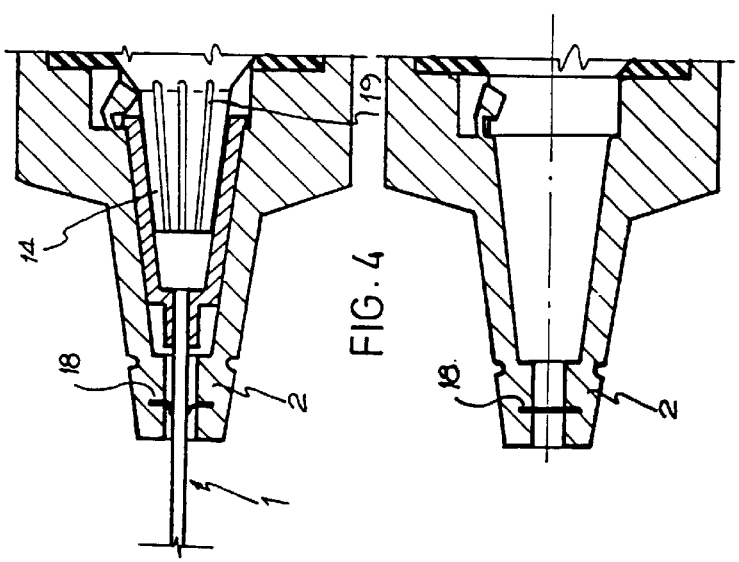
FIG. 4 shows, in two details, indicated as A in FIG. 1, the behavior of the elastic membrane positioned in the needle guide and proposed as a complementary variant, together with the drainage grooves made in the frustoconical tip of the plunger.

In the sequence illustrated in FIG. 4, it is possible to see the membrane 18 through which the tube of the needle 1 passes and which later seals off the guide orifice when the guide has moved away, the first diagram also showing the presence of the grooves 19 for draining off the minimal remains of liquid retained at the end of the path of the plunger.

Figure 5:
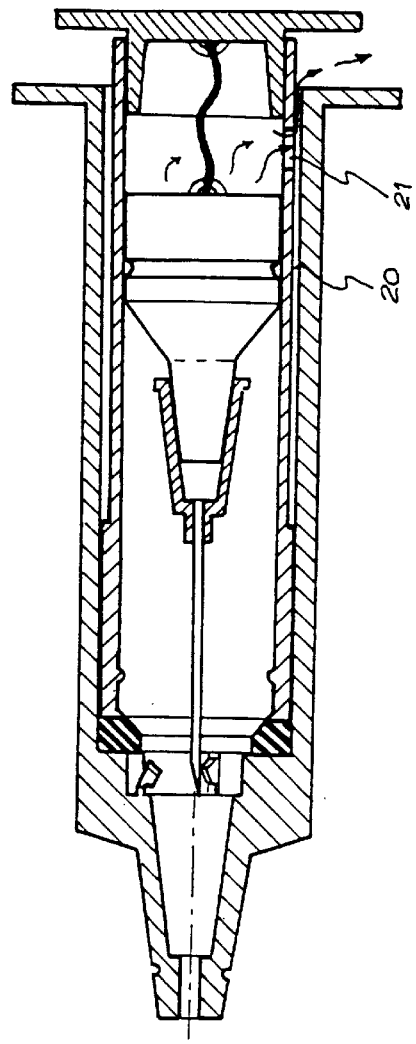
FIG. 5 shows a syringe like the invented syringe, with a plunger which has a reduced diameter in its rear portion and a complementary air-escape orifice.

The contents of both the preceding figure and of FIG. 5 show the complementary alternatives offered, the last figure demonstrating a plunger with an external section which is reduced over its distal portion, which reduces the friction surface between it and the cylinder of the syringe, forming, by addition, a cylindrical chamber 20 which can be used to allow more air to exit via the orifices 21 of the body of the plunger.

When implementing the disposable syringe with an automatically retractable hypodermic needle, which is described and illustrated by examples, it will be possible to incorporate modifications which must be regarded as variant embodiments included within the scope of protection of the present patent of invention, said scope being defined, fundamentally, by the text of the following claims.

We claim:

1. A disposable syringe with an automatically retractable hypodermic needle of the type consisting of an injector plunger, a container cylinder with needle-carrier head and a needle with connection ferrule, wherein said ferrule is housed in an inner hollow of the head of the cylinder, wherein the tube of the needle has passing axially through it a guiding channel to the outside, said hollow having a plurality of elastic retention tabs and the rear face of the needle-carrier head of the cylinder being in contact with an elastomeric washer interposed in an annular manner between it and the plunger which is defined by a cover whose attack front part has a slightly conical circular crown coinciding with said elastomeric washer and which is equipped centrally with a frustoconical core coinciding in a closely fitting manner with the opening of the ferrule of the needle, said cover also having a perimeter groove on its surrounding face which can be locked in terms of position in a plurality of domed projections of the inner wall of the tube which contains it, thereby forming the shaft of the plunger, the head of the cover and the base of said shaft being joined together by a tensioned elastic means and comprising, in the rear zone of their surrounding wall, a plurality of grooves in the rear zone which link its inside to the outside space.

2. A disposable syringe with an automatically retractable hypodermic needle as claimed in claim 1, wherein the guide orifice of the tube of the needle has a transverse elastic membrane which can be perforated by the discharge tube of the needle.

3. A disposable syringe with an automatically retractable hypodermic needle as claimed in claim 1, wherein the frustoconical tip of its plunger has a plurality of longitudinal grooves in its outer face, providing communication between the chamber of the cylinder and the opening of the ferrule of the needle when the latter comes into contact with said frusto-conical tip.

4. A disposable syringe with an automatically retractable hypodermic needle as claimed in claim 1, wherein the tube of the plunger has an external diameter which is reduced over its rear portion and has at least one through-orifice, in its surrounding wall, positioned close to its distal end.

* * * * *